United States Patent
Strayer et al.

(10) Patent No.: US 11,813,281 B2
(45) Date of Patent: Nov. 14, 2023

(54) METHODS FOR IMPROVING EXERCISE TOLERANCE IN MYALGIC ENCEPHALOMYELITIS PATIENTS

(71) Applicant: AIM ImmunoTech Inc., Ocala, FL (US)

(72) Inventors: David R. Strayer, Ocala, FL (US); Diane L. Young, Ocala, FL (US); Thomas K. Equels, Ocala, FL (US)

(73) Assignee: AIM ImmunoTech Inc., Ocala, FL (US)

( * ) Notice: Subject to any disclaimer, the term of this patent is extended or adjusted under 35 U.S.C. 154(b) by 48 days.

(21) Appl. No.: 17/413,387

(22) PCT Filed: Nov. 25, 2019

(86) PCT No.: PCT/US2019/063048
§ 371 (c)(1),
(2) Date: Jun. 11, 2021

(87) PCT Pub. No.: WO2020/123136
PCT Pub. Date: Jun. 18, 2020

(65) Prior Publication Data
US 2022/0062321 A1    Mar. 3, 2022

Related U.S. Application Data

(60) Provisional application No. 62/778,935, filed on Dec. 13, 2018.

(51) Int. Cl.
*A61K 31/713* (2006.01)
*A61K 47/61* (2017.01)
*A61K 47/64* (2017.01)
*A61P 21/06* (2006.01)

(52) U.S. Cl.
CPC ............ *A61K 31/713* (2013.01); *A61K 47/61* (2017.08); *A61K 47/645* (2017.08); *A61P 21/06* (2018.01)

(58) Field of Classification Search
CPC ...... A61K 31/713; A61K 47/645; A61P 25/00

USPC .............. 435/6.1, 91.1, 91.31, 455, 458; 514/44 A; 536/23.1, 24.5
See application file for complete search history.

(56) References Cited

U.S. PATENT DOCUMENTS

| 4,024,222 | A | 5/1977 | Ts'o et al. |
| 4,130,641 | A | 12/1978 | Ts'o et al. |
| 5,258,369 | A | 11/1993 | Carter |
| 8,722,874 | B2 | 5/2014 | Carter et al. |
| 9,315,538 | B2 | 4/2016 | Carter et al. |
| 2012/0195960 | A1* | 8/2012 | Wong ............ A61K 45/06 514/44 A |

FOREIGN PATENT DOCUMENTS

| WO | 2010/042229 A2 | 4/2010 | |
| WO | WO-2010042229 A2 * | 4/2010 | ......... A61K 31/7105 |
| WO | 2010/104571 A2 | 9/2010 | |
| WO | 2015/010022 A2 | 1/2015 | |

OTHER PUBLICATIONS

Mitchell, W.M. (Expert Rev Clin Pharmacol. vol. 9, No. 6, pp. 755-770 (2016)) (Year: 2016).*
William M. Mitchell, "Efficacy of rintatolimod in the treatment of chronic fatigue syndrome/myalgic encephalomyelitis (CFS/ME)", Expert Review of Clinical Pharmacology, 2016, pp. 755-770, vol. 9, No. 6.
International Search Report issued in PCT/US2019/063048; dated Mar. 16, 2020.
Written Opinion issued in PCT/US2019/063048; dated Mar. 16, 2020.
International Preliminary Report On Patentability (Chapter I) issued in PCT/US2019/063048; dated Jun. 8, 2021.

* cited by examiner

*Primary Examiner* — Jane J Zara
(74) *Attorney, Agent, or Firm* — Studebaker & Brackett PC

(57) ABSTRACT

The present invention relates to methods for treating a subject with myalgic encephalomyelitis/chronic fatigue syndrome symptoms comprising administering a target subject a pharmaceutical composition comprising a therapeutic dsRNA (tdsRNA).

16 Claims, 3 Drawing Sheets

METHODS FOR IMPROVING EXERCISE TOLERANCE IN MYALGIC ENCEPHALOMYELITIS PATIENTS

CROSS-REFERENCE TO RELATED APPLICATIONS

This application is a the U.S. National Stage of International Application No. PCT/US2019/063048 filed Nov. 25, 2019, which claims benefit of priority to U.S. Provisional Application No. 62/778,935 filed Dec. 13, 2018, the entire contents of which is incorporated herein by reference.

BACKGROUND

Myalgic Encephalomyelitis/Chronic Fatigue Syndrome (ME/CFS) is a debilitating disorder characterized by an incapacitating fatigue that is not improved by bed rest and includes a diverse combination of variable signs and symptoms. The majority of patients are women. The etiologic/pathogenic basis for ME/CFS is unknown and may be multifactorial with a variety of microbes, hormonal, and immunological abnormalities linked to its pathogenesis and dependent on genetic signatures.

BRIEF DESCRIPTION

The present disclosure provides methods for identifying and treating a subpopulation of ME/CFS patients, referred to herein as target subjects, that is responsive to treatment to a therapeutic dsRNA (tdsRNA). The methods and compositions of the present disclosure also find use in screening subjects for clinical trials and facilitating treatment decisions for a subject.

One embodiment is directed to a method for treating a subject with myalgic encephalomyelitis/chronic fatigue syndrome symptoms. The method comprises two steps. The first step involves determining that the subject is a target subject who exhibits onset of ME/CFS symptoms between about 2 to about 8 years prior to treatment. The second step involves administering to the target subject a pharmaceutical composition comprising as an active ingredient an effective amount of a therapeutic dsRNA (tdsRNA). One of the insights of this disclosure is that a target subject who exhibits onset of ME/CFS symptoms between about 2 to about 8 years is more responsive to treatment with tdsRNA.

Another aspect is directed to a method of this disclosure (e.g., the method described above), wherein the target subject exhibits onset of ME/CFS symptoms between about 2 to about 8 years and Post-Exertional Malaise (PEM) lasting about 24 hours or longer.

Another aspect is directed to a method of this disclosure (e.g., the method described above), wherein treating results in increasing exercise tolerance by a clinically significant amount of at least a 25% increase after treatment in the target subject as compared to prior to treatment.

Another aspect is directed to a method of this disclosure (e.g., the method described above), wherein at least 40% to 50% or more of the target subjects show an increase exercise tolerance of at least 25%.

Another aspect is directed to a method of this disclosure (e.g., the method described above), wherein administering is administering buccally; by implantation; by inhalation; by instillation; by nebulization; by suppository; enterally; epicutaneously; intracranially; intradermally; intramuscularly; intranasally; intraorbitally; intraperitoneally; intrathecally; intratracheally; intravenously; intraventricularly; intravesically; orally; parenterally; subcutaneously; sublingually; topically; transdermally; transmucosally; or a combination thereof.

Another aspect is directed to a method of this disclosure (e.g., the method described above), wherein the pharmaceutical composition is administered to the subject one to three times a week at a dosage which will provide on average of about 25-700 milligram per treatment day of tdsRNA for up to one month; longer than one month; up to one year; or longer than one year.

Another aspect is directed to a method of this disclosure (e.g., the method described above), wherein the pharmaceutical composition is administered to the subject intravenously one to three times a week at a dosage which will provide on average of about 25-700 milligram per treatment day of tdsRNA continuously for at least one month or longer than one month; up to one year; or longer than one year. "Per treatment day" is sometimes shortened to "per day" in this specification.

Another aspect is directed to a method of this disclosure (e.g., the method described above), wherein the subject is a human.

Another aspect is directed to a method of this disclosure (e.g., the method described above), wherein the therapeutic dsRNA is at least one dsRNA selected from the group consisting of $rI_n \cdot ribo(C_4U)_n$; $rI_n \cdot ribo(C_5U)_n$; $rI_n \cdot ribo(C_6U)_n$; $rI_n \cdot ribo(C_7U)_n$; $rI_n \cdot ribo(C_8U)_n$; $rI_n \cdot ribo(C_9U)_n$; $rI_n \cdot ribo(C_{10}U)_n$; $rI_n \cdot ribo(C_{11}U)_n$; $rI_n \cdot ribo(C_{12}U)_n$; $rI_n \cdot ribo(C_{13}U)_n$; $rI_n \cdot ribo(C_{14}U)_n$; $rI_n \cdot ribo(C_{15}U)_n$; $rI_n \cdot ribo(C_{16}U)_n$; $rI_n \cdot ribo(C_{17}U)_n$; $rI_n \cdot ribo(C_{18}U)_n$; $rI_n \cdot ribo(C_{19}U)_n$; $rI_n \cdot ribo(C_{20}U)_n$; $rI_n \cdot ribo(C_{21}U)_n$; $rI_n \cdot ribo(C_{22}U)_n$; $rI_n \cdot ribo(C_{23}U)_n$; $rI_n \cdot ribo(C_{24}U)_n$; $rI_n \cdot ribo(C_{25}U)_n$; $rI_n \cdot ribo(C_{26}U)_n$; $rI_n \cdot ribo(C_{27}U)_n$; $rI_n \cdot ribo(C_{28}U)_n$; $rI_n \cdot ribo(C_{29}U)_n$; $rI_n \cdot ribo(C_{30}U)_n$; $rI_n \cdot ribo(C_{31}U)_n$; $rI_n \cdot ribo(C_{32}U)_n$; $rI_n \cdot ribo(C_{33}U)_n$; $rI_n \cdot ribo(C_{34}U)_n$; $rI_n \cdot ribo(C_{35}U)_n$; $rI_n \cdot ribo(C_{4-29}U)_n$; $rI_n \cdot ribo(C_{4-30}U)_n$; $rI_n \cdot ribo(C_{11-14}U)_n$; $rI_n \cdot ribo(C_{14-30}U)_n$; $rI_n \cdot ribo(C_{30-35}U)_n$; $r(I)_n \cdot r(C_{30-35}U)_n$; and rugged dsRNA; and wherein n is an integer from 40 to 50,000. That is, for example, the tdsRNA is about n basepairs long.

Another aspect is directed to a method of this disclosure (e.g., the method described above), wherein the therapeutic dsRNA contains a minimum of 90 weight percent of dsRNA which is larger than a size selected from the group consisting of: 40 basepairs; 50 basepairs; 60 basepairs; 70 basepairs; and 80 basepairs.

Another aspect is directed to a method of this disclosure (e.g., the method described above), wherein the therapeutic dsRNA contains a minimum of 90 weight percent of dsRNA which is smaller than a size selected from the group consisting of: 10,000 basepairs; 9000 basepairs; 8000 basepairs; and 7000 basepairs.

Another aspect is directed to a method of this disclosure (e.g., the method described above), wherein the therapeutic dsRNA has about 4 to about 5000 helical turns of duplexed RNA strands.

Another aspect is directed to a method of this disclosure (e.g., the method described above), wherein the therapeutic dsRNA has a molecular weight from about 10 kilodaltons to about 30,000 kilodaltons.

Another aspect is directed to a method of this disclosure (e.g., the method described above), wherein the therapeutic dsRNA comprises a Rugged dsRNA and the Rugged dsRNA, as a weight percent of total RNA in the pharmaceutical composition, is greater than a value selected from the group consisting of: 1 weight percent; 5 weight percent; 10 weight percent; 20 weight percent; 30 weight percent; 40 weight percent; 50 weight percent; 60 weight percent; 70 weight percent; 80 weight percent; and 90 weight percent.

Another aspect is directed to a method of this disclosure (e.g., the method described above), wherein the tdsRNA is complexed with a stabilizing polymer. For example, the polymer may be selected from the group consisting of polylysine; polylysine plus carboxymethylcellulose; polyarginine; polyarginine plus carboxymethylcellulose; poly ICLC; and a combination thereof.

DETAILED DESCRIPTION

Definitions tdsRNA

Figure 1:
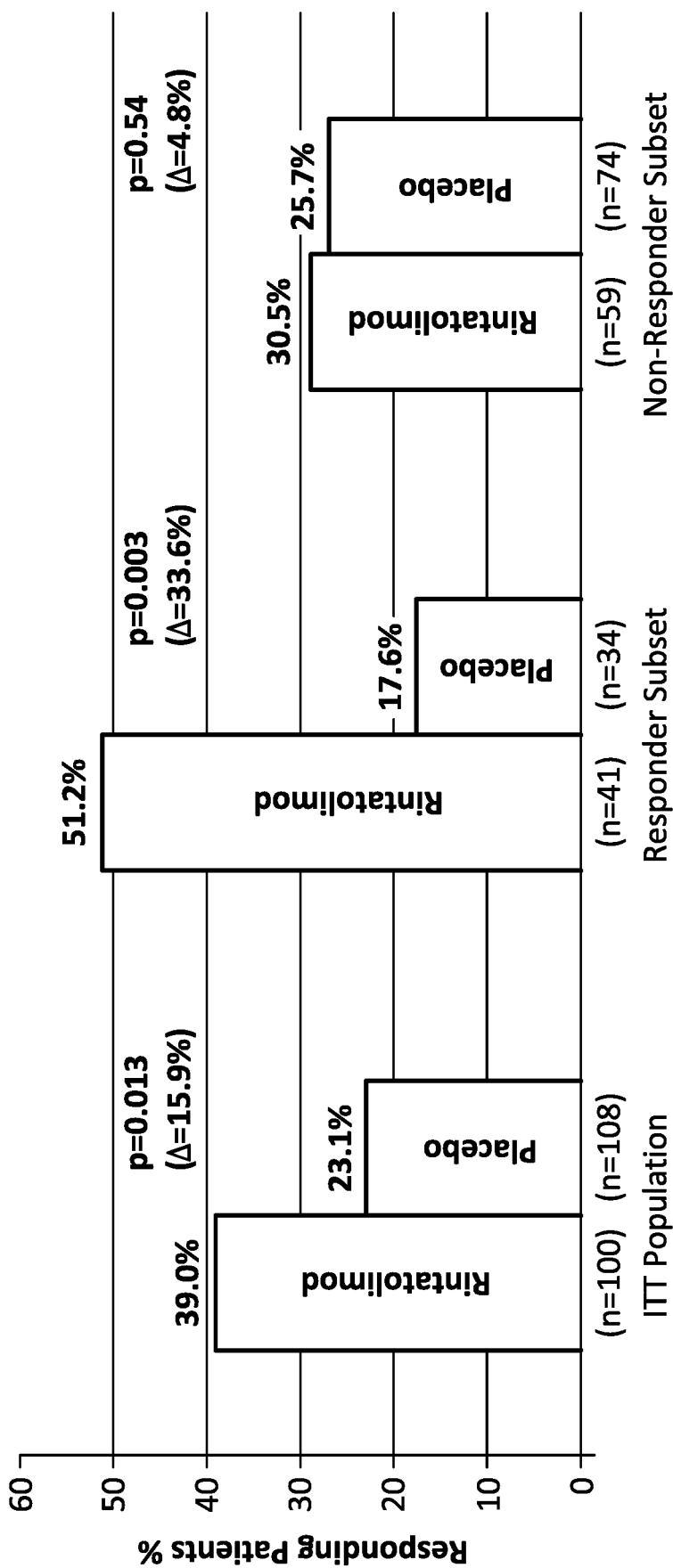
FIG. 1 depicts ME/CFS patients with greater than 25% increase in exercise treadmill tolerance (EU) from baseline at week 40. p-values derived from Chi-squared test.

This disclosure is directed to in part to a dsRNA referred to as a therapeutic dsRNA (tdsRNA) of which the preferred embodiments are rintatolimod (e.g., AMPLIGEN®); rugged dsRNA; a mismatched dsRNA; or dsRNA produced under a procedure listed in this disclosure. The tdsRNA has the properties described below.

For this disclosure, tdsRNA may refer to any dsRNA discussed in this disclosure and especially for any dsRNA disclosed in this section.

One embodiment of tdsRNA is rintatolimod. Rintatolimod (e.g., Poly I:Poly $C_{12}U$) is a synthetic double-stranded ribonucleic acid in which uridylic acid (U) substitution in the cytidylic chain creates a region of non-hydrogen bonding in the molecular configuration. The chemical name is polyriboinosinic: polyribocytidylic(12:1)uridylic acid. Rintatolimod is also trademarked as AMPLIGEN® and, in this disclosure, AMPLIGEN® and rintatolimod has the same meaning.

Poly I:Poly $C_{12}U$ is a structural analog of the polyribonucleotide complex consisting of polyriboinosinic acid hydrogen-bonded with polyribocytidylic acid, Poly I:Poly C. In the Poly C strand, uridylic acid substitutions occur on an average of every 12 to 13 bases, producing a duplex Poly I:Poly $C_{12}U$, containing specifically configured regions interspersed with uninterrupted regions. The single-stranded RNA (ssRNA) raw materials, Poly I and Poly $C_{12}U$, are annealed under controlled conditions to form the double-stranded RNA (dsRNA) rintatolimod (Poly I:Poly $C_{12}U$) molecules.

Another embodiment(s) of tdsRNA is a specific type of mismatched dsRNA as described as follows: The mismatched dsRNA may be of the general formula $rI_n \cdot r(C_{11-14}U)_n$, which is preferably $rI_n \cdot r(C_{12}U)_n$. The formula $rI_n \cdot r(C_{11-14}U)_n$ represents a double-stranded RNA with one strand being represented by $rI_n$ and the other strand represented by $(C_{11-14}U)_n$, wherein the dot symbol "·" represents that the two strands are hybridized to form a double-stranded RNA structure. It should be noted that while we referred to the two strands being hybridized, not 100% of the bases form base pairing as there are mismatches.

$rI_n$ represents polyriboinosine of n bases. "r" represents the RNA-like form of inosine which is riboinosine. This is as opposed to 2'-deoxyinosine. n represents the total length of this single-stranded inosine molecule—a single-stranded RNA.

For example, $r(C_{11-14}U)_n$ represents a single-stranded RNA which comprises C bases and U bases with the ratio of C bases to U bases being for every eleven to fourteen C there is a single U. "n" represents the total length, in bases, of this single-stranded RNA.

$rI_n \cdot r(C_{11-14}U)_n$, therefore, represents a double-stranded RNA with $rI_n$ hybridized to $r(C_{11-4}U)_n$. Since n represents the length for both strands, both strands of ssRNA are the same length which gives rise to a dsRNA with no significant single-stranded regions in the middle or at the end of the double-stranded structure.

In this disclosure, absent indications otherwise, all the polynucleotides administered to a patient is dsRNA or chemical analogs thereof such as riboinosine (i.e., RNA and not DNA unless otherwise indicated). "n" is the length of the dsRNA (in bases) and n is an integer having a value of from 40 to 50,000; 10 to 40,000; 10 to 500; 10 to 50 or 40-500 (rugged dsRNA). In this and the other formulas that follow r=ribo and rI=inosine.

Other mismatched dsRNAs for use in the present invention are based on co-polynucleotides such as poly $(C_m,U)$ or poly $(C_m,G)$ in which m is an integer having a value of from 4 to 29 and are mismatched analogs of complexes of polyriboinosinic and polyribocytidylic acids, formed by modifying $rI_n \cdot rC_n$ to incorporate unpaired bases (uracil (U) or guanine (G)) within the polyribocytidylate $(rC_m)$ strand. Alternatively, the dsRNA may be derived from $r(I) \cdot r(C)$ dsRNA by modifying the ribosyl backbone of polyriboinosinic acid $(rI_n)$, e.g., by including 2'-O-methyl ribosyl residues. The mismatched dsRNA may be complexed with an RNA-stabilizing polymer such as lysine carboxy methyl cellulose, or poly ICLC as described in the next paragraph. Of these mismatched analogs of $rI_n \cdot rC_n$, the preferred ones are of the general formula $rI_n \cdot r(C_{11-14}, U)_n$ and are described by Ts'o & Carter in U.S. Pat. Nos. 4,024,222 and 4,130,641; the disclosures of which are hereby incorporated by reference. The dsRNAs described therein are generally suitable for use according to the present invention.

Another aspect relates to specifically configured dsRNA derived from ribo(I)·ribo(C) dsRNA by modifying the ribosyl backbone of poly(riboinosinic acid) ribo$(I_n)$, e.g., by including 2'-0-methylribosyl residues. Specifically configured dsRNA may also be modified at the molecule's ends to add a hinge(s) to prevent slippage of the base pairs, thereby conferring a specific bioactivity in solvents or aqueous environments that exist in human biological fluids. The specifically configured dsRNA described in U.S. Pat. Nos. 4,024,222; 4,130,641; and 5,258,369 (incorporated by reference) are generally suitable as starting materials after selection for rugged dsRNA. While this disclosure describes Rugged dsRNA, the other dsRNAs described in this disclosure (including tdsRNA) which are not Rugged dsRNA are still suitable starting material for the production of Rugged dsRNA. In any embodiment, tdsRNA, including Rugged dsRNA, may be complexed with a stabilizing polymer such as polylysine, polylysine plus carboxymethylcellulose, polyarginine, polyarginine plus carboxymethylcellulose, or any combination thereof.

Other examples of mismatched dsRNAs for use as tdsRNA include: $rI_n \cdot ribo(C_4U)_n$, ratio of C to U in one strand is 4:1; $rI_n \cdot ribo(C_5U)_n$, ratio of C to U in one strand is 5:1; $rI_n \cdot ribo(C_6U)_n$, ratio of C to U in one strand is 6:1; $rI_n \cdot ribo(C_7U)_n$, ratio of C to U in one strand is 7:1; $rI_n \cdot ribo(C_8U)_n$, ratio of C to U in one strand is 8:1; $rI_n \cdot ribo(C_9U)_n$, ratio of C to U in one strand is 9:1; $rI_n \cdot ribo(C_{10}U)_n$, ratio of C to U in one strand is 10:1; $rI_n \cdot ribo(C_{11}U)_n$, ratio of C to U in one strand is 11:1; $rI_n \cdot ribo(C_{12}U)_n$, ratio of C to U in one strand is 12:1; $rI_n \cdot ribo(C_{13}U)_n$, ratio of C to U in one strand is 13:1; $rI_n \cdot ribo(C_{14}U)_n$, ratio of C to U in one strand is 14:1; $rI_n \cdot ribo(C_{15}U)_n$, ratio of C to U in one strand is 15:1; $rI_n \cdot ribo(C_{16}U)_n$, ratio of C to U in one strand is 16:1; $rI_n \cdot ribo(C_{17}U)_n$, ratio of C to U in one strand is 17:1; $rI_n \cdot ribo(C_{18}U)_n$, ratio of C to U in one strand is 18:1; $rI_n \cdot ribo(C_{19}U)_n$, ratio of C to U in one strand is 19:1; $rI_n \cdot ribo(C_{20}U)_n$, ratio of C to U in one strand is 20:1; $rI_n \cdot ribo(C_{21}U)_n$, ratio of C to U in one strand is 21:1; $rI_n \cdot ribo(C_{22}U)_n$, ratio of C to U in one strand is 22:1; $rI_n \cdot ribo(C_{23}U)_n$, ratio of C to U in one strand is 23:1; $rI_n \cdot ribo(C_{24}U)_n$, ratio of C to U in one strand is 24:1; $rI_n \cdot ribo(C_{25}U)_n$, ratio of C to U in one strand is 25:1; $rI_n \cdot ribo(C_{26}U)_n$, ratio of C to U in one strand is 26:1; $rI_n \cdot ribo(C_{27}U)_n$, ratio of C to U in one strand is 27:1; $rI_n \cdot ribo(C_{28}U)_n$, ratio of C to U in one strand is 28:1; $rI_n \cdot ribo(C_{29}U)_n$, ratio of C to U in one strand is 29:1; $rI_n \cdot ribo(C_{4-29}U)_n$ ratio of C to U in one strand is 4-29:1; $rI_n \cdot ribo(C_{4-29}G)_n$ ratio of C to G in one strand is 4-29:1; $rI_n \cdot r(C_{11-14}U)_n$ ratio of C to U in one strand is 11-14:1; $rI_n \cdot ribo(C_{12}U)_n$ ratio of C to U in one strand is 12:1; $rI_n \cdot ribo(C_{30}U)_n$ ratio of C to U in one strand is 30:1; and $rI_n \cdot ribo(C_{30-35}U)_n$ ratio of C to U in one strand is 30-35:1.

Briefly, tdsRNA is a type of dsRNA as described below. It is understood that if one strand is n in length the other strand will also be n in length even if it is not stated. Also, each intermediate value of the ratio is also claimed where a range is claimed.

For example, $rI_n \cdot ribo(C_{4-29}U)_n$ may encompass individually: $rI_n \cdot ribo(C_4U)_n$, $rI_n \cdot ribo(C_5U)_n$, $rI_n \cdot ribo(C_6U)_n$, $rI_n \cdot ribo(C_7U)_n$, $rI_n \cdot ribo(C_8U)_n$, $rI_n \cdot ribo(C_9U)_n$, $rI_n \cdot ribo(C_{10}U)_n$, $rI_n \cdot ribo(C_{11}U)_n$, $rI_n \cdot ribo(C_{12}U)_n$, $rI_n \cdot ribo(C_{13}U)_n$, $rI_n \cdot ribo(C_{14}U)_n$, $rI_n \cdot ribo(C_{15}U)_n$, $rI_n \cdot ribo(C_{16}U)_n$, $rI_n \cdot ribo(C_{17}U)_n$, $rI_n \cdot ribo(C_{18}U)_n$, $rI_n \cdot ribo(C_{19}U)_n$, $rI_n \cdot ribo(C_{20}U)_n$, $rI_n \cdot ribo(C_{21}U)_n$, $rI_n \cdot ribo(C_{22}U)_n$, $rI_n \cdot ribo(C_{23}U)_n$, $rI_n \cdot ribo(C_{24}U)_n$, $rI_n \cdot ribo(C_{25}U)_n$, $rI_n \cdot ribo(C_{26}U)_n$, $rI_n \cdot ribo(C_{27}U)_n$, $rI_n \cdot ribo(C_{28}U)_n$, and $rI_n \cdot ribo(C_{29}U)_n$.

As another example, $rI_n \cdot ribo(C_{30-35}U)_n$ will encompass individually: $rI_n \cdot ribo(C_{30}U)_n$, $rI_n \cdot ribo(C_{31}U)_n$, $rI_n \cdot ribo(C_{32}U)_n$, $rI_n \cdot ribo(C_{33}U)_n$, $rI_n \cdot ribo(C_{34}U)_n$, and $rI_n \cdot ribo(C_{35}U)_n$.

That is, each of the above molecules is also individually claimed as part of the invention and individually viewed as an embodiment.

Specifically-configured tdsRNA may be of the general formula $ribo(I_n) \cdot ribo(C_{4-29}U)_n$, $ribo(I_n) \cdot ribo(C_{11-14}U)_n$, or $ribo(I_n) \cdot ribo(C_{12}U)_n$, wherein the strands are comprised of ribonucleotides (ribo) and n is an integer from about 40 to about 40,000. For example, a strand comprised of poly (ribocytosinic$_{4-29}$ribouracilic acid), poly(ribocytosinic$_{11-14}$ribouracilic acid), or poly(ribocytosinic$_{12}$ribouracilic acid) may be partially hybridized to an opposite strand comprised of poly(riboinosinic acid) such that the two strands form an RNA double helix (dsRNA) that is not paired at the uracil base (i.e., mismatch).

For a subject (e.g., 150 lb or 70 Kg human) the dose of dsRNA may range from 0.1 to 1,000,000 µg, preferably from 0.4 to 400,000 µg.

The mismatched dsRNA may be administered by any known administration method (see, e.g., detailed description of "Administering Methods" for a more detailed listing).

Formulations for administration include aqueous solutions, syrups, elixirs, powders, granules, tablets and capsules which typically contain conventional excipients such as binding agents, fillers, lubricants, disintegrants, wetting agents, suspending agents, emulsifying agents, preservatives, buffer salts, flavoring, coloring and/or sweetening agents. They may be applied nasally with a spray or nebulizer. It will be appreciated that the preferred route will vary with the condition and age of the recipient, the nature of the infection or condition, and the chosen active ingredient.

In another aspect, the mismatched dsRNA can be a rugged dsRNA (see, e.g., U.S. Pat. Nos. 8,722,874 and 9,315,538). In one aspect, a rugged dsRNA can be an isolated double-stranded ribonucleic acid (dsRNA) which is resistant to denaturation under conditions that are able to separate hybridized poly(riboinosinic acid) and poly(ribocytosinic acid) strands, wherein only a single strand of said isolated dsRNA comprises one or more uracil or guanine bases that are not base-paired to an opposite strand and wherein said single strand is comprised of poly (ribocytosinic$_{30-35}$uracilic acid). Further, the single strand may be partially hybridized to an opposite strand comprised of poly(riboinosinic acid). In another aspect, rugged dsRNA may be an isolated double-stranded ribonucleic acid (dsRNA) which is resistant to denaturation under conditions that are able to separate hybridized poly(riboinosinic acid) and poly(ribocytosinic acid) strands, wherein said isolated dsRNA is comprised of $ribo(I_n) \cdot ribo(C_{30-35}U)_n$, in which ribo is a ribonucleotide and n is an integer from 40 to 500 or 40 to about 40,000. In another aspect, rugged dsRNA may be an isolated double-stranded ribonucleic acid (dsRNA) enzymatically active under thermal stress comprising: each strand with a molecular weight of about 250 kDa to about 320 kDa, a single strand comprised of poly(ribocytosinic$_{4-29}$uracilic acid) and an opposite strand comprised of poly(riboinosinic acid), wherein the two strands do not base pair the position of the uracil base, wherein the two strands base pair the position of the cytosine base, and wherein said strands are partially hybridized. In another aspect, rugged dsRNA may be an isolated double-stranded ribonucleic acid (dsRNA) enzymatically active under thermal stress comprising: each strand of a length from about 380 bases to about 450 bases, a single strand comprised of poly(ribocytosinic$_{4-29}$uracilic acid) and an opposite strand comprised of poly(riboinosinic acid), wherein the two strands do not base pair the position of the uracil base, wherein the two strands base pair the position of the cytosine base, and wherein said strands are partially hybridized. In another aspect, rugged dsRNA may be an isolated double-stranded ribonucleic acid (dsRNA) enzymatically active under thermal stress comprising: each strand with about 30 to 38 helical turns of duplexed RNA strands (dsRNA), a single strand comprised of poly(ribocytosinic$_{4-29}$uracilic acid) and an opposite strand comprised of poly(riboinosinic acid), wherein the two strands do not base pair the position of the uracil base, wherein the two strands base pair the position of the cytosine base, and wherein said strands are partially hybridized.

After synthesis, rugged dsRNA may be isolated by at least subjecting the partially hybridized strands of a population of dsRNA to conditions that denature most dsRNA (more than 10 wt % or mol %, more than 20 wt % or mol %, more than 30 wt % or mol %, more than 40 wt % or mol %, more than 50 wt % or mol %, more than 60 wt % or mol %, more than 70 wt % or mol %, more than 80 wt % or mol %, more than 90 wt % or mol %, more than 95 wt % or mol %, or more than 98 wt % or mol %) in the population, and then selection negatively or positively (or both) for dsRNA that remain partially hybridized. The denaturing conditions to unfold at least partially hybridized strands of dsRNA may comprise an appropriate choice of buffer salts, pH, solvent, temperature, or any combination thereof. Conditions may be empirically determined by observation of the unfolding or melting of the duplex strands of ribonucleic acid. The yield of rugged dsRNA may be improved by partial hydrolysis of longer strands of ribonucleic acid, then selection of (partially) hybridized stands of appropriate size and resistance to denaturation.

The purity of rugged dsRNA may thus be increased from less than about 0.1-10 mol % (e.g., rugged dsRNA is present in at least 0.1 mol % or 0.1 wt percent but less than about 10 mol % or 10 wt percent) relative to all RNA in the population after synthesis to a higher purity. A higher purity may be more than 20 wt % or mol %; more than 30 wt % or mol %; more than 40 wt % or mol %; more than 50 wt % or mol %; more than 60 wt % or mol %; more than 70 wt % or mol %; more than 80 wt % or mol %; more than 90 wt % or mol %; and more than 98 wt % or mol %. All wt % or mol % is relative to all RNA present in the same composition.

The molecular weight of rugged dsRNA may be from about 250 kDa to about 320 kDa, or from about 270 kDa to about 300 kDa. Lengths of a single or both strands of rugged dsRNA may be from about 380 bases to about 450 bases, or from about 400 bases to about 430 bases. The number of helical turns made by duplexed RNA strands of rugged dsRNA may be from about 30 to about 38, or from about 32 to about 36.

In another aspect, at least one or more different rugged dsRNA may be administered to a subject (e.g., human patient or animal) in need of such treatment.

The recommended dosage of mismatched dsRNA will depend on the clinical status of the subject and the physician's or veterinarian's experience treating the disease or other pathological condition. Mismatched dsRNA may be dosed at from about 0.5 mg to about 60 mg per day, from about 5 mg to about 400 mg per day, from 25 mg to about 700 mg per day, or from about 10 mg to about 800 mg per day in a subject (e.g., body mass of about 70-80 Kg for a human patient) on a schedule of either once a day up to 7 days weekly or once-weekly to thrice-weekly (preferably twice weekly), albeit the dose amount and/or frequency may be varied by the physician or veterinarian in response to the subject's symptoms. That is, for example, the administration may be in 50-1400 milligrams every other day leading to an average daily dosage of 25-700 milligrams per day.

The nucleic acid in solid form may be dissolved using known diluents for administration such as, for example, physiological phosphate-buffered saline, and then infused intravenously. It will be appreciated that the preferred dosage may vary with the age, condition, gender, or health status of the subject; the nature of the disease or other pathological condition, including the number and severity of symptoms; and the chosen active ingredient.

Case Definitions for Chronic Fatigue Syndrome

Two examples for determining if a patent has ME/CFS, which is also applicable to all aspects of this disclosure, are the diagnostic criteria as shown in TABLE 1 which is the 1988 Case Definition for Chronic Fatigue Syndrome or TABLE 2 which is the 1994 Case Definition for Chronic Fatigue Syndrome. The subjects (patients) that can be treated by the methods of the disclosure may be those that satisfy the 1988 definition of Chronic Fatigue Syndrome (TABLE 1); those that satisfy the 1994 definition of Chronic Fatigue Syndrome (TABLE 2); or those that satisfy both the 1988 definition and the 1994 definition of Chronic Fatigue Syndrome (TABLES 1 and 2); or those that satisfy other suitable case definitions, for example, 2003 Canadian Consensus Criteria for ME/CFS, 2015 IOM Diagnostic Criteria for ME/CFS, etc.

TABLE 1

1988 Case Definition for Chronic Fatigue Syndrome[1]

1. A new onset of persistent or relapsing, debilitating fatigue, or easy fatigability in a person who has no previous history of similar symptoms, that does not resolve with bedrest, and that is severe enough to reduce or impair average daily activity below 50% of the patient's premorbid activity level for a period of ≥6 months.
2. In addition, patient has:
A. 6 or more of the 11 symptom criteria and 2 or more of the physical criteria
OR
B. 8 or more of the 11 symptom criteria
Symptom Criteria mild fever (oral temp. 99.5-101.5° F.)[2]
sore throat
painful lymph nodes in the anterior or posterior cervical or axillary distribution
unexplained generalized muscle weakness
muscle discomfort or myalgia
prolonged (≥24 hours) generalized fatigue after levels of exercise that would
have been easily tolerated in the patient's premorbid state
generalized headaches[3]
migratory arthralgia without joint swelling or redness
neuropsychologic complaints[4]
sleep disturbance[5]
description of the main symptom complex as initially developing over a few hours to few days[6]
Physical Criteria (Physical criteria must be documented on at least two occasions, at least 1 month apart)
Low grade fever[7]
Nonexudative pharyngitis
Palpable or tender anterior or posterior cervical or axillary nodes[8]

[1]To fulfill a symptom criteria, a symptom must have begun at or after the time of onset of increased fatigability and must have persisted or recurred over a period of at least 6 months (individual symptoms may or may not have occurred simultaneously).
[2]Note: Oral temperatures of greater than 101.5° F. are less compatible with chronic fatigue syndrome and should prompt studies for other causes of illness.

TABLE 1-continued

1988 Case Definition for Chronic Fatigue Syndrome[1]

[3]Of a type, severity or pattern that is different from headaches the patient may have had in the premorbid state.
[4]One or more of the following: photophobia, transient visual scotomata, forgetfulness, excessive irritability, confusion, difficulty thinking, inability to concentrate, depression.
[5]Hypersomnia, insomnia, difficulty falling asleep or early morning awakening.
[6]This is not a true symptom, but may be considered as equivalent to the above symptoms in meeting the requirements of the case definition.
[7]Oral temperature between 99.7 and 101.5° F. or rectal temperature between 100.0 and 101.8° F.
[8]Note: Lymph nodes greater than 2 cm in diameter suggest other causes. Further evaluation is warranted.

TABLE 2

1994 Case Definition for Chronic Fatigue Syndrome

INCLUSION CRITERIA:

1. Unexplained persistent or relapsing chronic fatigue that is of new or definite onset (i.e., not lifelong), is not the result of ongoing exertion, is not substantially alleviated by rest, and results in substantial reduction in previous levels of occupational, educational, social, or personal activities.
2. The concurrent occurrence of four or more of the following symptoms, all of which must have persisted or recurred during 6 or more consecutive months of illness and must not have predated the fatigue.
Symptom Criteria substantial impairment in short-term memory or concentration[1]
sore throat
muscle pain
tender cervical or axillary lymph nodes
multi-joint pain without swelling or redness
headaches of a new type, pattern, or severity[2]
unrefreshing sleep
post-exertional malaise lasting more than 24 hours
EXCLUSION CRITERIA:

3. Any active medical condition that may explain the presence of chronic fatigue, such as untreated hypothyroidism, sleep apnea and narcolepsy, and iatrogenic conditions such as side effects of medication.
4. Any previously diagnosed medical condition whose clinical doubt and whose continued activity may explain the chronic fatiguing illness. Such conditions may include previously treated malignancies and unresolved cases of hepatitis B or C virus infection.
5. Any past or current diagnosis of a major depressive disorder with;
a. bipolar affective disorders
b. schizophrenia of any subtype
c. delusional disorders of any subtype
d. dementias of any subtype
e. anorexia nervosa
f. bulemia nervosa
6. Alcohol or other substance abuse within 2 years before the onset of the chronic fatigue and at any time afterward.
7. Severe obesity as defined by a body mass index equal to or greater than 45.

[1]Self-reported impairment in short-term memory or concentration severe enough to cause substantial reduction in previous levels of occupational, educational, social, or personal activities.
[2]Headache must be of a new type, severity or pattern that is different from headaches the patient may have had in the premorbid state.

Post-Exertional Malaise (PEM)

Post-Exertional Malaise is a cluster of symptoms that can include rapid muscular or cognitive fatigability, headaches, muscle aches, generalized weakness, cognitive deficits, insomnia, and swollen lymph nodes. These symptoms follow mental or physical exertion and last about 24 hours or more.

Pharmaceutical Composition

The pharmaceutical composition comprising one or more active agents listed above may be administered to a subject by any local or systemic route known in the art (see, e.g., detailed description of "Administering Methods" for a more detailed listing). The pharmaceutical composition and/or the active agents may be micronized by milling or grinding solid material, dissolved in a vehicle (e.g., sterile buffered saline or water) for injection or instillation (e.g., spray), topically applied, or encapsulated in a liposome or other carrier for targeted delivery. It will be appreciated that the preferred route may vary with the age, condition, gender, or health status of the subject; the nature of the disease or other pathological condition, including the number and severity of symptoms; and the chosen active ingredient.

Formulation

Formulations for administration (i.e., pharmaceutical compositions) may include aqueous solutions, syrups, elixirs, powders, granules, tablets, and capsules which typically contain conventional excipients such as binding agents, fillers, lubricants, disintegrants, wetting agents, suspending agents, emulsifying agents, preservatives, buffer salts, flavoring, coloring, and/or sweetening agents. It will be appreciated that the preferred formulation may vary with the age, condition, gender, or health status of the subject; the nature of the disease or other pathological condition, including the number and severity of symptoms; and the chosen active ingredient.

Medicament

In another aspect, a medicament (e.g., a pharmaceutical composition) containing the immune activator(s) is provided. Optional other components of the medicament include excipients and a vehicle (e.g., aqueous buffer or water for injection) packaged aseptically in one or more separate containers (e.g., nasal applicator or injection vial). Processes for using and making the medicament are also provided. Further aspects will be apparent from the following description and claims, and any generalizations thereto.

Effective Amount and Therapeutically Effective Amount

The compositions are delivered in effective amounts. The term "effective amount" refers to the amount necessary or sufficient to realize a desired biologic effect. Combined with the teachings provided herein, by choosing among the various active compounds and weighing factors such as potency, relative bioavailability, patient body weight, severity of disease, adverse side effects, and preferred mode of administration, an effective prophylactic or therapeutic treatment regimen can be planned which does not cause substantial toxicity and yet is effective to treat the particular subject. Also, based on testing, the toxicity of the inhibitor is expected to be low. The effective amount for any particular application can vary depending on such factors as the disease or condition being treated, the particular inhibitor being administered, the size of the subject, or the severity of the disease or condition. One of ordinary skill in the art can empirically determine the effective amount of a particular active ingredient without necessitating undue experimentation. It is preferred generally that a maximum dose be used, that is, the highest safe dose according to medical judgment.

For any compound described herein, the therapeutically effective amount can be initially determined from preliminary in vitro studies and/or animal models. A therapeutically effective dose can also be determined from human data for inhibitors that have been tested in humans and for compounds which are known to exhibit similar pharmacological activities, such as other related active agents. The applied dose can be adjusted based on the relative bioavailability and potency of the administered compound. Adjusting the dose to achieve maximal efficacy based on the methods described above and other methods are well known in the art, is well within the capabilities of the ordinarily skilled artisan.

Administering Methods

Suitable administration/treatment protocols for treating a subject include, for example, administering to the patient (subject) an effective amount of tdsRNA.

In some embodiments, the combination therapy of the invention comprises the administration of tdsRNA. Any compound or chemical or formulation in this disclosure may be administered by any of the administration methods disclosed. The tdsRNA may be administered in any suitable manner known in the art. For example, the tdsRNA may be administered sequentially (at different times) or in one dose or in a bolus. In some embodiments, the tdsRNA is administered continuously.

Dosing Period

A dosing period is usually about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 week, 2 weeks, 3 weeks, 4 weeks, one month longer than one month, one year, or longer than one year.

In certain embodiments, the tdsRNA is administered one dose per day, one dose every 2 days, one dose every 3 days, one dose every 4 days, one dose every 5 days, twice a week, once a week, once every two weeks, once every three weeks, once every four weeks, or once a month, or any value in between the recited values.

In specific aspects, the tdsRNA is administered, for example, at a dose from about 1 mg/kg to 10 mg/kg biweekly.

Dosing Amount

In certain embodiments, the tdsRNA is administered in a dose of about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, any value in between the recited values, or any range in between the recited values. Examples of a range would be between 4 to 20 mg/kg or between 6 to 20 mg/kg.

As additional examples of what is described above, the following ranges are also applicable and envisioned: about 0.1 mg/kg to about 30 mg/kg, about 0.1 mg/kg to about 20 mg/kg, about 0.1 mg/kg to about 10 mg/kg, about 0.1 mg/kg to about 8 mg/kg, about 0.1 mg/kg to about 7 mg/kg, about 0.1 mg/kg to about 6 mg/kg, about 0.1 mg/kg to about 5 mg/kg, about 0.1 mg/kg to about 4 mg/kg, about 0.1 mg/kg to about 3 mg/kg, about 0.2 mg/kg to about 3 mg/kg, about 0.3 mg/kg to about 3 mg/kg, about 0.4 mg/kg to about 3 mg/kg, about 0.6 mg/kg to about 3 mg/kg, about 0.8 mg/kg to about 3 mg/kg, about 0.1 mg/kg to about 2 mg/kg, about 0.1 mg/kg to about 1 mg/kg.

The total daily dose may vary from about 20 mg to about 800 mg, preferably about 50 mg to about 600 mg, most preferably about 100 mg to about 400 mg.

In certain embodiments, the tdsRNA is administered twice daily; daily; in a single dose per week, in two doses per week, in three doses per week, in four doses per week, in five doses per week, or in 6 or more doses per week.

In one embodiment, the tdsRNA is administered at a dose from about 0.50 mg/kg to 10 mg/kg twice weekly, weekly, every other week.

An effective amount of the tdsRNA may be administered for the prevention or treatment of chronic fatigue syndrome to reduce symptoms and/or to increase exercise tolerance or athletic performance. The appropriate dosage of the tdsRNA may be determined based on the symptoms to be treated, the type of the tdsRNA, the severity and course of the ME/CFS, the clinical condition of the subject, the subject's clinical history and response to the treatment, the symptoms involved, the subject's body mass, gender, immune status and the discretion of the attending physician. Suitable regimens can be selected by one skilled in the art by considering such factors.

Accordingly, in one embodiment, the dose of the tdsRNA is calculated as mg/kg body weight. However, in another embodiment, the dose of the tdsRNA is a flat fixed-dose that is fixed irrespective of the weight of the patient.

The tdsRNA may be administered by the same route of administration or by different routes of administration. For example, in some embodiments, the tdsRNA is administered buccally; by implantation; by inhalation; by instillation; by nebulization by suppository; enterally; epicutaneously; intracranially; intradermally; intramuscularly; intranasally; intraorbitally; intraperitoneally; intrathecally; intratracheally; intravenously; intraventricularly; intravesically; orally; parenterally; subcutaneously; sublingually; topically; transdermally; transmucosally; or a combination thereof.

Treat

The terms "treat", "treating", "treated" or "treatment", as used herein, refer to therapeutic treatment wherein the object is to eliminate or lessen symptoms. Beneficial or desired clinical results include, but are not limited to, elimination of symptoms, alleviation of symptoms, diminishment of the extent of the condition, stabilized (i.e., not worsening) state of condition, delay or slowing of progression of the condition.

Subject

As used herein, a "subject" is a mammal, preferably, a human. In addition to humans, categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include non-human primates, rats, mice, rabbits, guinea pigs, etc. In some aspects of this and other embodiments, the subject is a mammal. Preferably, the mammal is selected from the group consisting of humans, primates, farm animals, and domestic animals. More preferably, the mammal is a human. As used herein, the terms "patient" or "subject" are used interchangeably and mean a mammal, including, but not limited to, a human or non-human mammal, such as a bovine, equine, canine, ovine, or feline. Preferably, the patient is a human.

Reduce or Inhibit

By "reduce or inhibit" is meant the ability to cause an overall decrease of 20%, 30%, 40%, 50%, 60%, 70%, 75%, 80%, 85%, 90%, 95%, or greater. Reduce or inhibit can refer to the symptoms of the disorder being treated.

Ameliorate

As used herein, the terms "ameliorate", "ameliorating" and grammatical variations thereof mean to decrease the severity of the symptoms of a disease in a subject.

Effective Amount or Therapeutically Effective Amount

In the present invention, an "effective amount" or a "therapeutically effective amount" of a tdsRNA disclosed herein is an amount of such material that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of any active agent disclosed herein or a composition containing the same will be that amount of the active agent or composition, which is the lowest dose effective to produce the desired effect.

Overview

Introduction

Analysis of rintatolimod, a selective TLR3 agonist, in a double-blind, randomized, placebo-controlled trial demonstrated statistical significance ($p<0.05$) in the relief of fatigue as measured by exercise treadmill tolerance (EU). Rintatolimod is also trademarked as AMPLIGEN® and, in this disclosure, AMPLIGEN® and rintatolimod has the same meaning. The primary endpoint of exercise treadmill tolerance (ETT) has been re-examined as a function of the duration of myalgic encephalomyelitis/chronic fatigue syndrome symptoms prior to enrollment into the study.

Methods:

The Intent-to-Treat (ITT) population of 208 subjects (n=208) was separated into two subsets. The first subset contains subjects with ME/CFS symptoms, optionally including these subjects also have PEM lasting about 24 hours or longer, duration of ME/CFS symptoms for 2-8 years—there are a total of 75 subjects in this first subset (n=75). The second subset contains the subjects that do not fit the first subset. For example, the members of the second subset are those with ME/CFS symptom duration less than 2 years or greater than 8 years—there are a total of 133 subjects (n=133) in this second set.

Exercise treadmill duration and the vertical rise components of the exercise treadmill tolerance data based on the treadmill inclination were analyzed for a: Responder Subset where n=75;

b: Non-Responder Subset where n=133; and c: intent-to-treat population where n=75+133=208.

Results:

For the intent-to-treat population of 208 subjects, a significantly greater percentage of patients who received rintatolimod (39%) vs. placebo patients (23%) improved exercise treadmill duration of greater than or equal to 25% (p=0.013). For the subset of patients with baseline myalgic encephalomyelitis/chronic fatigue syndrome (ME/CFS) symptom duration of 2-8 years (i.e., Responder Subset), 51.2% vs. 17.6% of rintatolimod vs. placebo patients, respectively, improved exercise duration≥25% (p=0.003). Placebo adjusted improvement was 15.9% in the intent-to-treat population compared to 33.6% in the 2-8 year subset. The placebo adjusted percentage improvements in exercise duration and vertical rise for the 2-8 year subset were over twice that seen for the intent-to-treat population. The less than 2 years plus greater than 8 years subset (Non-Responder Subset, where n=133) failed to show any clinically significant exercise treadmill tolerance (EU) response to rintatolimod compared to placebo.

Analysis:

Analysis of exercise treadmill data from a double-blind, randomized, placebo-controlled study of rintatolimod has identified a subset of ME/CFS patients with a 2-8 year window of symptoms onset and with ≥2 fold greater exercise responses compared to the intent-to-treat (ITT) population. Substantial improvement in physical performance was seen for the majority of these severely debilitated patients (51.2%) who improved exercise duration by ≥25%. A ≥25% improvement in exercise duration was associated with clinically significant improvements in quality of life in this study population. Rintatolimod was generally well-tolerated in this population of patients suffering from severe ME/CFS.

EXAMPLES

Example 1: Production of a dsRNA

Synthesis of single-stranded poly(I) and poly($C_{12}U$) began with enzymatic polynucleotide synthesis of the polynucleotides from the respective nucleotides starting materials: inosine for poly(I); cytidine (C) and uridine (U) for poly($C_{12}U$). Then repetitive extraction and precipitation steps were used to remove residual impurities. The reaction solutions containing the products were concentrated by ultrafiltration and extracted with phenol. The concentrated and extracted solutions were precipitated, dissolved, and re-precipitated from aqueous ethanol (50:50). Enzymatic Synthesis. The enzymatic synthesis used in the manufacturing process is dependent on the enzyme polynucleotide phosphorylase to synthesize polyinosinic acid and polycytidilic$_{12}$uridilic acid from their respective starting materials: cytidine 5'-diphosphate, trisodium salt (CDP—Na$_3$), uridine 5'-diphosphate, disodium salt (UDP—Na$_2$) and inosine 5'diphosphate, trisodium salt (IDP—Na$_3$).

Equal molar amounts of the ssRNA were mixed in an annealing step, and cooled to room temperature. The solutions were sterile filtered.

If Rugged dsRNA or another fraction of dsRNA was desired, it is produced from an annealed dsRNA by high-performance liquid chromatography (HPLC). Rugged dsRNA's characteristics are defined in the other parts of this disclosure.

Example 2: Treating ME/CFS Subjects

Introduction

Severe ME/CFS subjects, in a clinical trial, demonstrated significant improvement in the primary endpoint, exercise treadmill tolerance (EU), following the systemic administration of rintatolimod. In this study, rintatolimod was administered twice weekly for 40 weeks while controlled subjects were administered placebo for 40 weeks.

This analysis of exercise treadmill tolerance (ETT) response in a subset (n=75) based primarily on baseline ME/CFS symptom duration reveals ≥2 fold higher placebo adjusted rintatolimod improvements compared to the intent-to-treat (ITT) population (n=208).

Methods

The study was a prospective, double-blind trial with equal parallel cohorts conducted to evaluate the safety and efficacy of rintatolimod in ME/CFS. Many of the ME/CFS patients (also referred to herein as subjects) were unable to physically perform the standard Bruce sub-maximal exercise protocol commonly used for the evaluation of cardiac function. For patient safety reasons a modified Bruce ME/CFS protocol was used that was similar in energy requirements to a Bruce protocol designed for the elderly. The primary endpoint was change in exercise treadmill tolerance (ETT) from baseline to Week 40.

These analyses used SAS (Version 9.2) statistical software (Cary, NC). All statistical analyses were two-sided. Exercise treadmill duration and vertical rise were analyzed using the two-sided Student's T-test. A comparison of the proportion of patients who improved exercise treadmill tolerance (EU) by at least 25% was analyzed using the Chi-squared test. Study participants were required to undergo exercise treadmill tolerance (EU) testing using a modified Bruce protocol which incorporated progressive increases in the treadmill inclination from 0% to 21% in seven 3% increments. The exercise treadmill tolerance (EU) testing protocol had a vertical component which was calculated for each of the inclination stages completed. The last stage attempted, which was usually only partially completed, was also included in the calculation based on the percentage of completion. The increase in vertical rise from baseline to Week 40 was calculated for each patient and was expressed as vertical feet "climbed".

Results

A cohort (Responder Subset) of the intent-to-treat (IU) population (n=208), based primarily on baseline ME/CFS symptom duration, was identified with twice the exercise treadmill tolerance (EU) response compared to the entire intent-to-treat (ITT) population. The Responder Subset consists of ME/CFS patients with symptom duration of disease of 2-8 years (n=75). The Non-Responder population consists of the subset of the intent-to-treat (ITT) population that did not meet the definition of the Responder Subset.

TABLE 3 illustrates the demographics of the Responder and Non-Responder Subsets. Mean age, age range, and gender were well matched between the Subsets and the original intent-to-treat (ITT) population. A significant difference was observed, however, in the two subsets for the duration of ME/CFS symptoms prior to initiation of rintatolimod/placebo dosing (p<0.001), as expected based on the selection criteria.

TABLE 3

Comparison of Demographics of intent-to-treat (ITT) Population to the Responder and Non-Responder Subsets

| Parameter | ITT Population (n = 208) | | Responder Subset (n = 75) | | Non-Responder Subset* (n = 133) | |
| --- | --- | --- | --- | --- | --- | --- |
| | Rintatolimod | Placebo | Rintatolimod | Placebo | Rintatolimod | Placebo |
| Number of ME/CFS Patients | 100 | 108 | 41 | 34 | 59 | 74 |
| Duration of ME/CFS Symptoms mean ± SD (years) | 9.5 ± 5.3 | 9.7 ± 6.2 | 5.0 ± 1.6 | 4.9 ± 1.9 | 12.5 ± 4.8 | 12.0 ± 6.2 |
| Mean age in years | 43 ± 9.3 | 43 ± 10.1 | 41 ± 9.4 | 41 ± 9.9 | 45 ± 9.0 | 45 ± 9.9 |
| Age Range | 20-60 | 19-60 | 20-59 | 19-58 | 24-60 | 22-60 |
| % Female | 70% | 77% | 71% | 79% | 70% | 76% |

*Non-Responder Subset consists of the remainder of the intent-to-treat (ITT) Population that is not included in the Responder Subset TABLE 4 illustrates the significant difference between the Responder Subset and Non-Responder Subset in treadmill endurance. The difference between the rintatolimod and placebo cohorts in the Responder Subset was 122.5 seconds compared to 30.1 seconds in the Non-Responder Subset and 67.5 seconds in the intent-to-treat (ITT) population The difference in exercise treadmill tolerance (EU) duration was statistically significant for the intent-to-treat (ITT) population with n=208 (p=0.043) and the Responder subset with n=75 (p=0.047).

TABLE 4

Comparison of Change from Baseline in Mean exercise treadmill tolerance (ETT) Duration (Seconds) at Week 40 for intent-to-treat (ITT) Population vs. the Responder and Non-Responder Subsets

| Cohort | Increase from Baseline - Seconds | | % Increase in Intra-Group Means | |
|---|---|---|---|---|
| | Rintatolimod | Placebo | Rintatolimod | Placebo |
| ITT Population n = 208 | 95.7 Δ = 67.5 p = 0.043* | 28.2 | 16.6 Δ = 11.8 | 4.8 |
| Responder Subset n = 75 | 146.7 Δ = 122.5 p = 0.047* | 24.2 | 27.8 Δ = 23.6 | 4.2 |
| Non-Responder Subset n = 133 | 60.2 Δ = 30.1 p = 0.44* | 30.1 | 9.8 Δ = 4.7 | 5.1 |

Δ = Difference between rintatolimod and placebo
*Student's T-test (2-sided)

TABLE 4 also illustrates the percent increase in intra-group mean exercise duration from baseline to Week 40. The placebo adjusted mean increase is shown following the Δ. The increase seen in the Responder subset (Δ=23.6%) is twice that seen for the intent-to-treat (ITT) population (Δ=11.8%).

These differences in response to rintatolimod are further illustrated in the responder analysis shown in FIG. 1. FIG. 1 depicts ME/CFS patients with greater than or equal to 25% increase in exercise treadmill tolerance (EU) from baseline at Week 40. In FIG. 1, the p-values are derived from Chi-squared test. The percentage of exercise treadmill tolerance (EU) responders (≥25% improvement in exercise duration) seen in the rintatolimod arm (39.0%) vs. placebo (23.1%) was statistically significant for the intent-to-treat (ITT) population (p=0.013). The majority of the patients receiving rintatolimod in the Responder subset (51.2%) were exercise treadmill tolerance (EU) responders vs, placebo (17.6%) (p=0.003). The placebo adjusted difference in percent responders shown below the p-value in FIG. 1 for the Responder subset (Δ=33.6%) is twice that seen for the intent-to-treat (ITT) population (Δ=15.9%). There was only a 4.8% difference seen for the Non-Responder subset (p=0.54). The value of a ≥25% increase was based on a request from the FDA (Division of Antiviral Drug Products) to establish a meaningful percent change that was above intra-patient exercise tolerance variability.

The exercise treadmill tolerance (EU) protocol included progressive increases in inclination from 0% to 21% in seven 3% increments. The vertical rise in feet was calculated for each subject. TABLE 5 shows the mean change in vertical rise from baseline to Week 40 for the intent-to-treat (ITT) population (n=208) and both subsets. The improvement in vertical rise in the intent-to-treat (ITT) population was significantly greater (p=0.033) for the rintatolimod cohort (56.9 feet) compared to the placebo cohort (22.5 feet).

TABLE 5

Comparison of Change from Baseline in Mean exercise treadmill tolerance (ETT) Vertical Rise (Feet) at Week 40 for intent-to-treat (ITT) Population vs. the Responder and Non-Responder Subsets

| Cohort | Increase from Baseline - Vertical Feet | | % Increase in Intra-Group Means | |
|---|---|---|---|---|
| | Rintatolimod | Placebo | Rintatolimod | Placebo |
| ITT Population n = 208 | 56.9 Δ = 34.4 p = 0.033* | 22.5 | 47.1 Δ = 28.6 | 18.5 |
| Responder Subset n = 75 | 85.2 Δ = 61.9 p = 0.050* | 23.3 | 91.0 Δ = 70.3 | 20.7 |
| Non-Responder Subset n = 133 | 37.3 Δ = 15.1 p = 0.401* | 22.2 | 26.6 Δ = 9.0 | 17.6 |

Δ = Difference between rintatolimod and placebo
*Student's T-test (2-sided)

The increase in vertical rise seen for the Responder Subset (n=75) was 85.2 feet for the rintatolimod cohort vs. 23.3 feet for the placebo cohort. The difference in vertical rise was 61.9 feet and was at the threshold for statistical significance (p=0.050). Nonetheless, the difference in percent increase in intra-group means between the rintatolimod and placebo cohorts seen for the Responder subset of 70.3% was over twice that seen for the intent-to-treat (ITT) population of 28.6%. The increases in vertical rise for the rintatolimod and placebo cohorts in the Non-Responder subset were 37.3 and 22.2 feet, respectively, which was not statistically significant (p=0.401).

Discussion

The Toll-Like Receptors (TLRs) act as a first line of defense against microbial pathogens by the induction of innate immunity and further provide the initial cellular orchestration for the induction of adaptive immune responses to provide specific humoral and cell-mediated immunity mediated in part by inflammatory cytokines. They can be found especially in dendritic cells (DCs), central in the host adaptive immune response system. All of the TLRs use a MyD88 dependent signaling pathway with the exception of TLR3 that uses the MyD88 independent TRIF pathway. Two other dsRNA activated inducers of gene expression that initiate innate immune responses are the cytosolic helicases, MDAS and RIG-1. Rintatolimod (Poly I:Poly $C_{12}U$) activity in the induction of innate and adaptive immunity is restricted to TLR-3 in contrast to other dsRNA activators of TLR3 (e.g.-Poly I:Poly C, viral dsRNA). The restriction of rintatolimod to TLR3 is responsible for the absence of systemic cytokine induction in primates including humans. Of significance to the aberrant immune responses observed in ME/CFS is a recent seminal observation in cancer that rintatolimod increases the ratio of Teff/Treg cells in the human microenvironment in contrast to the two non-restricted dsRNA TLR3 agonists discussed above.

Figure 2:
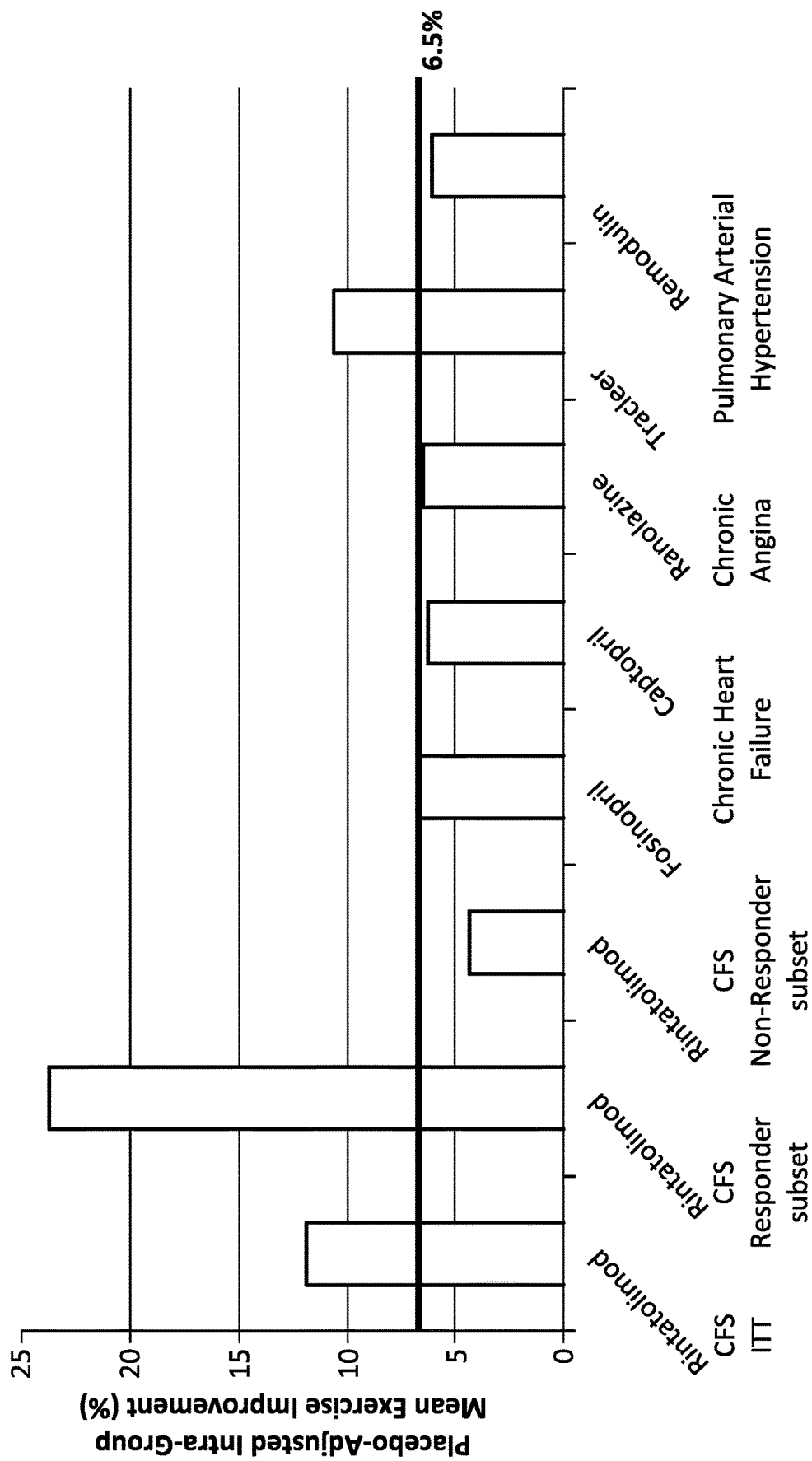
FIG. 2 depicts the Placebo-adjusted Percent Intra-Group Mean Exercise Improvements for Rintatolimod.

This analysis presented surprising and unexpected findings. That is, the subgroup of patients defined primarily by the length of ME/CFS symptoms (2-8 years) showed an increased likelihood of a clinically beneficial response to rintatolimod (FIG. 2). Cardiopulmonary exercise tolerance testing is an objective measure of efficacy for physical fatigue and is accepted as a regulatory standard for approval of drugs ameliorating exertional fatigue. Accordingly, at the request of the FDA, to define a clinically significant exercise treadmill tolerance (EU) improvement, based on prior FDA approvals for two drugs, Fosinopril and Captopril, for chronic heart failure using exercise tolerance testing (FIG. 2), ≥6.5% improvement in intra-group mean exercise tolerance was pre-specified in the protocol as showing efficacy of rintatolimod in ME/CFS. This protocol was reviewed by FDA and was authorized to proceed. Following the completion of the study, five drugs have now been approved by the FDA for improvement in exercise tolerance for congestive heart failure, chronic angina, or pulmonary hypertension (FIG. 2). FIG. 2 depicts the placebo-adjusted percent intra-group mean exercise improvements for rintatolimod: intent-to-treat (ITT) population and the responder subset exceed drugs approved for non-ME/CFS severe exertional fatigue. Four of the five provided 6.5% or less improvement in exercise tolerance. Tracleer, approved for pulmonary hypertension, provided 11% as compared to the rintatolimod intent-to-treat (ITT) population at 11.8% improvement. The Responder subset within the intent-to-treat (ITT) population with symptoms between 2-8 years had an increased response to rintatolimod with 23.6% improvement, which is over twice the clinical improvement/quality of life benefit observed for any of the 5 drugs approved by FDA.

The most important placebo-adjusted exercise tolerance responses observed with the 2-8 year responder subset vs. the intent-to-treat (ITT) population can be summarized as follows: (a) There is an increase in exercise duration over placebo (seconds) 67.5 (ITT) vs. 122.5 (2-8 year subset); (b) There is a percentage increase in net intra-group mean ETT duration 11.8 (ITT) vs. 23.6 (2-8 year subset); (c) There is a percentage patients with ≥25% net increase in ETT duration 15.9 (ITT) vs. 33.6 (2-8 year subset); (d) There is a percentage increase in net intra-group mean vertical rise (feet) 28.6 (ITT) vs. 70.3 (2-8 year subset)

Rintatolimod is a dsRNA (Poly I:Poly $C_{12}U$) that functions as an activating ligand for TLR3. The introduction of uridine, which does not base-pair with inosine, into the polycytidine chain creates a mismatched region in the dsRNA and restricts the activity of rintatolimod to a TLR3 agonist with no activation of the cytosolic helicases. The importance of this unique property of rintatolimod as a restricted TLR3 agonist is a reduction of systemic inflammatory cytokines that has limited the clinical utility of other TLR3-activating ligands, such as Poly I:Poly C, that also activate MDAS and RIG-1. Other TLR-activating agonists that use the inflammatory cytokine inducing MyD88-dependent pathway of intracellular signaling also induce greater levels of toxicity compared to rintatolimod.

In order to maintain direct comparability between rintatolimod clinical trials, only those ME/CFS subjects who met the inclusion criteria utilizing the original 1988 criteria of the CDC have been evaluated for efficacy and safety. Patients enrolled in the trial met both the CDC 1988 diagnostic criteria and the more relaxed 1994 CDC case definition. An international consortium proposed in 2011 that Myalgic Encephalomyelitis was a preferable term for the syndrome complex. Profound fatigue remains as the core descriptor for all definitions. The rintatolimod clinical trials have focused on the alleviation of that core symptom and its effect on the quality of life.

Rintatolimod administered by intravenous infusion has been generally well-tolerated. The most frequent adverse event is a flu-like syndrome consisting of headache, chills, fever, flushing, and myalgia that occurs in approximately 44-45% of rintatolimod patients vs. 30-33% of placebo patients.

In this study, rintatolimod is clearly active for the improvement of exercise tolerance and quality of life in a subset of patients with ME/CFS. Severely debilitated ME/CFS patients receiving rintatolimod in this study with a 25% improvement in exercise duration, also demonstrated a corresponding clinically significant improvement in two quality of life secondary endpoints, Karnofsky Performance Score (KPS) and Vitality Score (SF-36). The Vitality Score increased from 9.49 at baseline to 24.10 at week 40, a 14.6 point increase, and almost three times the minimum clinically important difference (MCID) of 5 points. The Vitality Score is one of the best SF-36 subscales for measuring the reduction in functioning seen in patients with CFS. The median KPS increased from 50 to 60, a 10 point improvement. A 10 point increase in KPS was pre-specified as a clinically significant improvement. An increase in KPS from 50 to 60 indicates that a patient, who, at a KPS of 50, required considerable assistance from a caregiver to complete their required daily activities (i.e., bathing, dressing, grooming, food preparation, eating, etc.), now having a KPS of 60 only required occasional assistance (once or twice weekly) for these same daily activities. Importantly, these improvements, a 10 point increase in KPS and a 14.6 point increase in Vitality Score, are both clinically relevant and represent objective improvements in quality of life.

Figure 3:
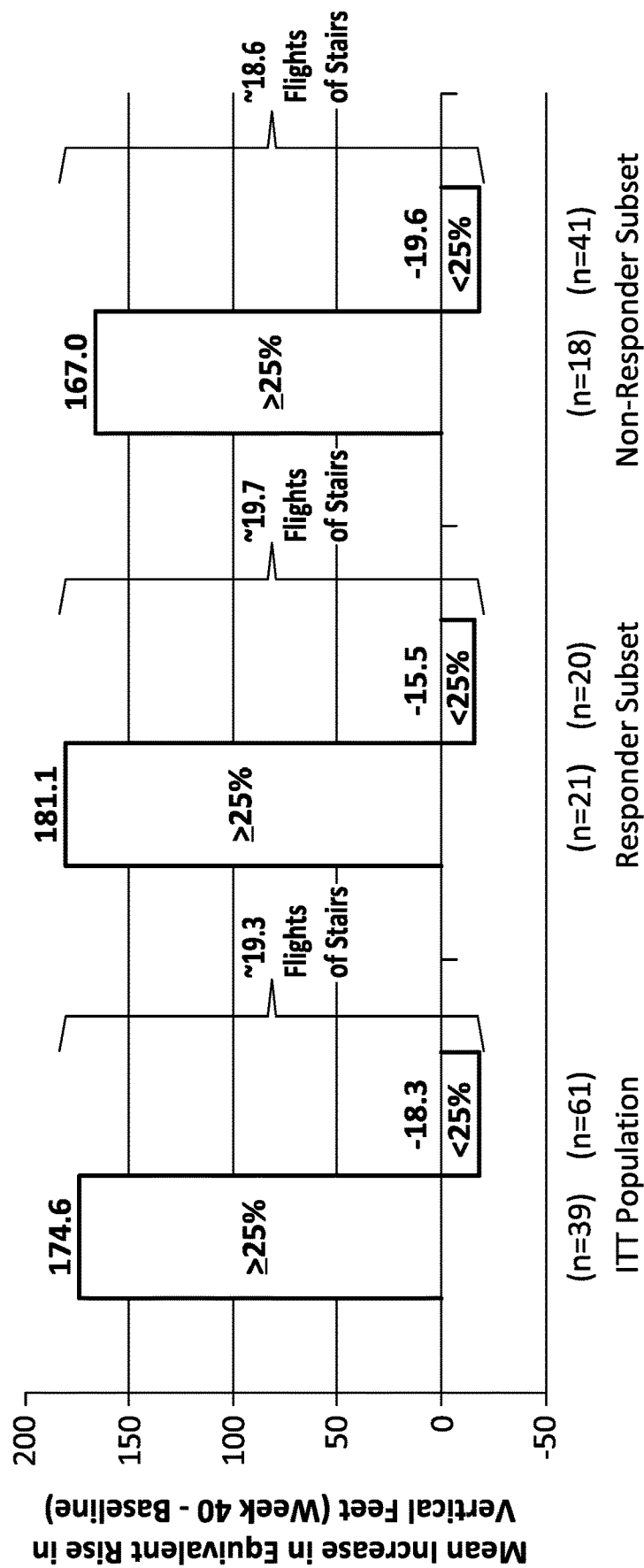
FIG. 3 depicts Rintatolimod treated patients by exercise treadmill tolerance (EU) Response (greater than or equal to 25% vs. less than 25%).

A majority (51.2%) of patients in the 2-8 year Responder subset improved exercise treadmill tolerance (EU) by ≥25%. What does a ≥25% improvement in exercise treadmill tolerance (EU) duration mean with regard to a real-life situation? For example, what improvement in the ability to climb stairs could be possible for severely debilitated ME/CFS subjects who improve ≥25% in exercise treadmill tolerance (EU) duration? FIG. 3 shows rintatolimod treated patients by exercise treadmill tolerance (EU) response (≥25% vs. <25%) comparing change from baseline to Week 40 in vertical rise in feet for the intent-to-treat (IU) population and both subsets. In both the intent-to-treat (ITT) population and Responder subset (FIG. 3) the difference between exercise treadmill tolerance (EU) responders (≥25% increase) and non-responders (<25% increase) was that exercise treadmill tolerance (EU) responders had an ability to climb an equivalent of ~19 more flights of stairs or ~190 vertical feet more than the non-responders (assuming ~10 feet/flight of stairs).

For the intent-to-treat (ITT) population (n=100), 39% of the patients improved exercise treadmill tolerance (EU) by ≥25% and those patients were able to climb the equivalent of 174.6 more vertical feet at Week 40 compared to baseline. This increase in ~175 vertical feet was on average accomplished over approximately 6-8 additional minutes on the treadmill at inclinations between 12-21%. The patients who did not improve by at least 25% had a mean decrease in the ability to climb by 18.3 feet. Similar results were seen for the Responder subset with 51.2% of these patients improving exercise treadmill tolerance (EU) by ≥25% (181.1 vertical feet). Even patients in the Non-Response subset with ≥25% exercise treadmill tolerance (EU) improvement were able to climb about 167 additional vertical feet. Thus, overall, patients with a ≥25% improvement in exercise treadmill tolerance (EU) were able to climb a mean of approximately 17.5 more flights of stairs compared to baseline. Rintatolimod treatment significantly increased the number of these responders in the intent-to-treat (ITT) population (p=0.013) and in the Responder subset (p=0.003) compared to placebo (FIG. 1). An ability to climb a mean of approximately 18 additional flights of stairs, as seen in FIG. 3, by the majority of patients (51.2%) in the Responder subset (FIG. 1), who improved exercise treadmill tolerance (EU) by ≥25%, represents a substantial improvement in quality of life.

Rituximab, a monoclonal antibody, which binds to CD20 expressed on B-cells, was originally reported in an open-label trial as active in ME/CFS. A 152 patient double-blind, placebo-controlled clinical trial in Norway initiated in 2015 has been reported as failing to have met its endpoint. To our knowledge, no other drug or biologic is in advanced clinical development for ME/CFS. Rintatolimod is approved for ME/CFS in Argentina with market access anticipated in the near future.

The presence of a differential response to rintatolimod based on the duration of symptoms of ME/CFS shows that rintatolimod is a core drug with clear activity in a subset of patients suffering from ME/CFS.

In this specification, stating a numerical range, it should be understood that all values within the range are also described (e.g., one to ten also includes every value between one and ten as well as all intermediate ranges such as two to ten, one to five, and three to eight). The term "about" may refer to the statistical uncertainty associated with a measurement or the variability in a numerical quantity which a person skilled in the art would understand does not affect the operation of the invention or its patentability.

All modifications and substitutions that come within the meaning of the claims and the range of their legal equivalents are to be embraced within their scope. A claim which recites "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative and not restrictive because the scope of the legal protection provided for the invention will be indicated by the appended claims rather than by this specification.

INCORPORATION BY REFERENCE

All publications, patent applications, and patents mentioned herein are hereby incorporated by reference in their entirety as if each individual publication or patent was specifically and individually indicated to be incorporated by reference. In case of conflict, the present application, including any definitions herein, will control.

We claim:

1. A method for treating a subject with myalgic encephalomyelitis/chronic fatigue syndrome symptoms, the method comprising:
    determining that the subject is a target subject who exhibits onset of ME/CFS symptoms between 2 to 8 years prior to treatment; and
    administering to the target subject a pharmaceutical composition comprising as an active ingredient an effective amount of a therapeutic dsRNA (tdsRNA);
    wherein the tdsRNA is $rI_n \cdot r(C_{12}U)_n$ and
    wherein n is an integer from 40 to 50,000.

2. The method of claim 1 wherein the target subject exhibits onset of ME/CFS symptoms between 2 and 8 years and Post-Exertional Malaise (PEM) lasting about 24 hours or longer.

3. The method of claim 1, wherein treating results in increasing exercise tolerance by a clinically significant amount of at least a 25% increase after treatment in the target subject as compared to prior to treatment.

4. The method of claim 1, wherein at least 40% to 50% or more of the target subjects show an increase exercise tolerance of at least 25%.

5. The method of claim 1, wherein administering is selected from the group consisting of administering buccally; administering by implantation; administering by inhalation; administering by instillation; administering by nebulization; administering by suppository; administering enterally; administering epicutaneously; administering intracranially; administering intradermally; administering intramuscularly; administering intranasally; administering intraorbitally; administering intraperitoneally; administering intrathecally; administering intratracheally; administering intravenously; administering intraventricularly; administering intravesically; administering orally; administering parenterally; administering subcutaneously; administering sublingually; administering topically; administering transdermally; administering transmucosally; and a combination thereof.

6. The method according to claim 1, wherein the pharmaceutical composition is administered to the subject one to three times a week at a dosage which will provide on average of about 25-700 milligram per treatment day of tdsRNA for up to one month; longer than one month; up to one year; or longer than one year.

7. The method according to claim 1, wherein the pharmaceutical composition is administered to the subject intravenously one to three times a week at a dosage which will provide on average of about 25-700 milligram per treatment day of tdsRNA continuously for at least one month; longer than one month; up to one year; or longer than one year.

8. The method of claim 1, wherein the subject is a human.

9. The method of claim 1,
    wherein the tdsRNA further comprises rugged dsRNA.

10. The method of claim 1, wherein the tdsRNA contains a minimum of 90 weight percent of dsRNA which is larger than 40 basepairs.

11. The method of claim 1, wherein the tdsRNA contains a minimum of 90 weight percent of dsRNA which is smaller than 10,000 basepairs.

12. The method of claim 1, wherein the tdsRNA has about 4 to about 5000 helical turns of duplexed RNA strands.

13. The method of claim 1, wherein the tdsRNA has a molecular weight from about 10 kilodaltons to about 30,000 kilodaltons.

14. The method of claim 1, wherein the tdsRNA comprises a Rugged dsRNA and the Rugged dsRNA, as a weight percent of total RNA in the pharmaceutical composition, is greater than 1 weight percent.

15. The method of claim 1, wherein the tdsRNA is complexed with a stabilizing polymer.

16. The method of claim 15, wherein the stabilizing polymer is selected from the group consisting of polylysine; polylysine plus carboxymethylcellulose; polyarginine; polyarginine plus carboxymethylcellulose; poly ICLC; and a combination thereof.

* * * * *